US011404151B2

(12) United States Patent
Sandvik et al.

(10) Patent No.: US 11,404,151 B2
(45) Date of Patent: Aug. 2, 2022

(54) MEDICAL PACKAGE, SYSTEM AND METHOD FOR MANAGING MEDICAL PACKAGE

(71) Applicant: Tridentify AB, Gothenburg (SE)

(72) Inventors: Leif Sandvik, Hono (SE); Christian Strandberg, Gustafsberg (SE); Thomas Oskarsson, Västra Frölunda (SE); Magnus Gramming, Bankeryd (SE)

(73) Assignee: Tridentify AB, Gothenburg (SE)

( * ) Notice: Subject to any disclaimer, the term of this patent is extended or adjusted under 35 U.S.C. 154(b) by 407 days.

(21) Appl. No.: 15/061,420

(22) Filed: Mar. 4, 2016

(65) Prior Publication Data

US 2016/0200515 A1 Jul. 14, 2016

Related U.S. Application Data

(63) Continuation-in-part of application No. 13/993,130, filed as application No. PCT/SE2011/051366 on Nov. 15, 2011, now abandoned.

(30) Foreign Application Priority Data

Dec. 16, 2010 (SE) .................................. 1001195-5

(51) Int. Cl.
*G16H 20/13* (2018.01)
*G05B 15/02* (2006.01)

(52) U.S. Cl.
CPC ............. *G16H 20/13* (2018.01); *G05B 15/02* (2013.01)

(58) Field of Classification Search
CPC ................................. G16H 20/13; G05B 15/02

(Continued)

(56) References Cited

U.S. PATENT DOCUMENTS 7,041,941 B2 * 5/2006 Fanes, Jr. ................ G06F 19/00
219/413
7,564,364 B2 * 7/2009 Zweig .................... G01K 1/024
340/588

(Continued)

FOREIGN PATENT DOCUMENTS

WO 2006108026 10/2006
WO 2007014147 2/2007

OTHER PUBLICATIONS

Extended European Search Report for corresponding Application No. 11854112.7 dated Dec. 21, 2016.

*Primary Examiner* — Luna Champagne
(74) *Attorney, Agent, or Firm* — Renner, Otto, Boisselle & Sklar, LLP

(57) ABSTRACT

System for handling medical packages provided with at least one unique identifier and other relevant information. The system includes at least one tracking device arranged to accompany said package from the entry of the package in the system to a decision on administration of the package-specific product content to a recipient. The tracking device comprises an integrated data logger that records data on at least one environmental parameter affecting remaining lifetime of the product content, a calculation function that calculates a value for the remaining lifetime, and an integrated indicator device showing if the product content has a remaining useful lifetime. The tracking device has a unique device identity that can be read and associated with said unique identity code and the other relevant information so that all relevant data concerning the product content can be handled and transferred between system devices without risk of confusion.

34 Claims, 4 Drawing Sheets

(58) Field of Classification Search
USPC .......................................................... 705/28
See application file for complete search history.

(56) References Cited

U.S. PATENT DOCUMENTS

| | | | | |
|---|---|---|---|---|
| 7,926,322 B1* | 4/2011 | Queen | ................ | G01N 21/6408 |
| | | | | 73/1.02 |
| 7,990,270 B2* | 8/2011 | Mostov | ................ | G06Q 10/08 |
| | | | | 340/500 |
| 8,542,099 B2* | 9/2013 | Pizzuto | ................ | H04Q 9/00 |
| | | | | 340/10.1 |
| 2002/0013523 A1 | 1/2002 | Csore et al. | | |
| 2003/0052788 A1 | 3/2003 | Kwong-Tai Chung | | |
| 2003/0069796 A1 | 4/2003 | Elwood et al. | | |
| 2004/0044326 A1 | 3/2004 | Kranz et al. | | |
| 2004/0046020 A1* | 3/2004 | Andreasson | ........ | G07F 17/0092 |
| | | | | 235/385 |
| 2004/0166583 A1 | 8/2004 | De Gaulle et al. | | |
| 2004/0247016 A1 | 12/2004 | Faries et al. | | |
| 2005/0066961 A1* | 3/2005 | Rand | ................... | A61M 15/009 |
| | | | | 128/200.14 |
| 2005/0184149 A1* | 8/2005 | Auchinleck | ......... | G06F 19/3481 |
| | | | | 235/385 |
| 2007/0001862 A1 | 1/2007 | Zweig | | |
| 2007/0028642 A1* | 2/2007 | Glade | ................... | A45C 11/20 |
| | | | | 62/371 |
| 2008/0262646 A1* | 10/2008 | Breed | ................. | G07C 5/0808 |
| | | | | 700/226 |
| 2009/0109033 A1* | 4/2009 | Salvat | ................... | G01S 5/0027 |
| | | | | 340/572.1 |
| 2010/0076507 A1* | 3/2010 | Jones | ...................... | F03G 5/06 |
| | | | | 607/2 |
| 2010/0231358 A1* | 9/2010 | Mello | ................... | G06Q 30/06 |
| | | | | 340/10.1 |
| 2014/0367256 A1* | 12/2014 | Terashima | ............. | G16H 10/60 |
| | | | | 204/403.01 |

* cited by examiner

MEDICAL PACKAGE, SYSTEM AND METHOD FOR MANAGING MEDICAL PACKAGE

RELATED APPLICATIONS

This application is a continuation-in-part of U.S. patent application Ser. No. 13/993,130 filed Jun. 11, 2013 which is a national phase of International Application No. PCT/SE2011/051366 filed Nov. 15, 2011 which claims priority to Swedish Provisional Application No. 1001195-5 filed on Dec. 16, 2010. The entire disclosures of these applications are hereby incorporated by reference.

TECHNICAL AREA

The present invention relates to a medical package, a system and a method for managing the medical package, especially bags containing blood products such as blood and blood plasma, vaccines and packages. The system according to the invention can also be used for managing other types of packaging with a product content that requires special storage conditions for sustainability to be assured.

BACKGROUND OF INVENTION

Manufacturing, transportation, storage, administration and handling of various medical products, such as blood, blood plasma and vaccines, it is absolutely important that the contents of each package can be identified in a safe manner.

It is also essential to ensure that such medical products are transported and stored under conditions which ensure that they are not adversely affected or destroyed before being administered to a patient or other recipient. Such storage conditions are accomplished usually by the medical package wherever possible be kept in special refrigerators or cold rooms under strict control of temperature, light, moisture, contamination risk, etc.

If one considers that there is a risk that a medical package has been exposed to inappropriate storage conditions, such as an excessively low or high storage temperature, or may have been exposed to contamination, e.g. by the bed of a patient, this package with its product content must be discarded. In the case of blood products has, for example, the EU and national health authorities have started to formulate stronger demands for an improved control over the lifecycle before being administered to the intended recipients.

There are different systems for marking, identification and management of medical products such as blood and blood plasma. This kind of products are generally packaged in bags fitted with a suitable labeling related to product content and other relevant information concerning the product in question. At the site in which the medical products are manufactured and/or filled in their packaging, an operator labels each package with all of data necessary for its use, such as an identification code, date of filling and a specification of the packaged product content. After transportation of the filled package to a unit in which the package must be stored and/or packaged product content must be used, another operator must interpret the labeling and product data listed on the package and enter the data in a local storage system. In the previously known systems, particularly at smaller storages or care and treatment units paper-based and even handwriting-based input of data related to inventory management still exists. An unclear or incomplete manual entry of product data in a storage management system makes it difficult to find required specific package of the product content. An incorrect manual entry of data into a storage management system can at worst results in a risk of confusion between two specific medical packages with various product content and/or different useful life-times.

In the current systems, every movement of packages between various devices, such as between a manufacturing unit and a depot, from a depot and a care facility, or between a cold store and a refrigerator adjacent to an operating theatre, often requires a manual input of several data records for each individual package unit in a variety of storage systems, without requiring users of the systems therefore receive any comprehensive or complete picture of their stock for a specific medical product or the exact storage location of a specific package with the specific product content as required in a specific case. The people who use the current systems are often not accustomed to complex storage management systems and may have difficulty coping with the manual entries of data in the manner required for the systems to function as intended. Besides the fact that incorrect or incomplete entries of data represent a security risk, they can also results in unnecessary discarding of the package. The unclear situation of stocks which easily can follow the current system fragmented structure and manual data entry leads to spending a lot of time for storage inventory and search for specific products and will also result in many unnecessary movements between the various units where medical packages are stored and handled.

In connection with the transport and storage of medical packages, there is, as mentioned earlier, also a risk that the products are subjected to an adverse environmental impact, such as too high temperature, which can results in a shorter shelf lifetime and destruction of a packaged product content. Today's system has often no complete control over which specific medical package that may have been exposed to such adverse environmental impact, which of course is very risky from the product safety point of view. Besides the increased risk for recipients to indicate what the contents of packages should be used for, the lack of control over the remaining life of the individual packages in the system leads to a large number of unnecessary rejections of products. For example, it is common for staff to collect 10 blood bags before surgery and 8 of these blood bags are administered to the patient during surgery. After the operation, 2 of the blood bags are still unused and could perhaps be used for another suitable patient, but with today's system thus must still be discarded for safety reasons because of the lack of knowledge about how the blood in these blood bags have been stored and transported after the bags left the manufacturing or the refilling unit.

U.S. 2004/166583 concerns a method which consists in determining ageing an ageing index of a blood bag, to determine whether the blood bag is or not suitable for transfusion to a patient. The ageing index is regularly calculated at the blood transfusion center from the sample, until it is removed from storage. The present invention differs from this document in two independent elements: the package is provided with a code and other information, and that the indicator is located on the tracking device and not the location of the system where the package is stored, as in this document.

U.S. 2004/044326 relates to a method for detection of bags containing biological fluids. The method comprises the steps of: obtaining a sterile bag for storage of biological fluids; placing a variety of biological fluids in the bag, providing a first information processing device with a data input device and a data transmission device that can write data that has been placed in the information processing device, a chip for storing data in a way that can be read by a second information processing device; provide bag with a readable/writable data storage chip; collecting fluid data on the biological fluid, and entering data, such as fluid data, to the first information processing device for data transfer to the chip. Data storage chip is capable of interaction with the first and second information processing devices. The first information processing unit writes data to data storage chip and the second information processing device can read data from the chip. The procedure of this document does not provide a visual readout of a unique identifier of a package if it would be necessary or no linkage of the unique identity code on the package with a unique device identity of a tracking device that comes with the package. Moreover, it appears that the process according to this document does not allow any visual readout of any marking on the tracking/data chip supplied with the package. Furthermore, it is not clear from the document, that the described procedure would allow the tracking/data storage chip to be cleaned and reused, which is possible with tracking devices in the system according to the present invention.

SUMMARY OF THE INVENTION

A first object of the invention is therefore to provide a system for handling medical packages that makes it possible to eliminate the above mentioned problems.

The invention also provides a reliable sensor-based real-time temperature monitoring system for medical products, such as blood bags. The system is versatile and can be used both for the current quality information and monitoring changes over time and show position. The system can ensure quality, traceability and availability of the product/blood all the time. The system is also recyclable, which leads to lower costs and meets the growing demand for waste minimization.

This first objective is achieved with a system according to claim 1, wherein each package is provided with at least one unique identifier and other relevant information that identifies and characterizes a specific product content of the package in a unique, for the use of that specific product content, required way, whereby the system includes at least one tracking device which is arranged to accompany the package with the specific product content over a period of time that extends from the entry of the package into the system to a possible decision on administration of that specific product content to an intended recipient, whereby the tracking device includes an integrated data logger, which is arranged to register data about at least one ambient parameter affecting that specific product contents remaining lifetime during the same period, whereby the tracking device includes a calculation function, which based on the logged data and time calculates an amount of remaining lifetime, whereby the tracking device includes an integrated indicator device which is arranged to indicate to an operator, at least if the specific product content has remaining useful lifetime or not, and whereby the tracking device has a unique device identity that can be read and the system associated with the unique identifier and the other relevant information on that package to ensure that all relevant data relating to said specific product content, both data input by the operator and the data generated by the data logger of that tracking device or other system devices in the system, can be handled and transferred between the system devices without risk of confusion.

The system for handling medical package according to the invention ensures, using the tracking device according to the invention, that packages and data related to their product content are not confused during management of the system. Thanks to the logging of environmental parameters by using the tracking device that comes with each package, a complete verification that all the packages in the system still have an estimated remaining useful lifetime is achieved. The system according to the invention ensures that a required package with a specific product content always can be identified quickly and without confusion, that this specific product content is still useful when it is administered, and reduces the number of unnecessary rejections, as the system operators have a clear indication of the status of product content in a specific package when the package is handled in the system.

A second object of the invention is to provide a system for handling medical package that makes it possible to record the relevant data for a specific new medical package and a new specific product content in the system in a user-friendly and safe manner, and then be able to follow this particular package and this specific product content for the continued management of the system.

This second objective is achieved with a system according to patent claim 13 where the other system devices in the system includes at least one access point, for the entry of new medical package in the system, provided with means for reading the unique identifier and the other relevant information on a specific package and means for transmitting the identifier and information to at least one data record in a database included in the system, and means for reading said unique device identity of a tracking device that will accompany that specific package to the continued management of the system and means for transmitting said unique device identification to said database for interconnection with said data record or data records.

Thanks to means for reading the unique identity code and other relevant information on a specific package of the access point, means for sensing the unique device identity of the included tracking device and a means to transfer of all this information into a database where all the related information should be associated, the system operators' workload and the risk of incorrect data entry in the system is reduced, since the number of stations where data on package and/or product content must be entered manually into the system by an operator is minimized.

A third object of the invention is to provide a system for handling medical package that allows system users to be able to find a specific package or a specific product content as requested, to follow this specific package's or this specific product content's movement and current location in the system and to obtain information about an estimated expiration date for the specific product content of a specific package, from a selectable spot by one of the users.

This third objective is achieved with a system according to patent claim 13, where the aforementioned other system devices in the system include at least one portal for system user who can communicate with at least one data server that stores data relating to all medical package that is entered into the system, whereby the data stored in said data server at least includes: a unique identifier for each specific package that is entered into the system, a unique device identity of the specific tracking device enclosed with this specific package in the management of the system, a latest reading date of the information concerning the specific package that is stored in the data server; a specification of the last access point to the specific tracking device, and thus the specific package has passed in the system, an estimated expiration date for a specific product content in the specific package, and other relevant information that identifies and characterizes the specific product content in a unique, for use the specific product content necessary way, the data system users may access from at least one user terminal connected to the portal for system users.

Thanks to the provision of the portal for the system users, the system users can from a selectable spot access all the data required for identification, tracking, positioning, ordering, transportation, quality assessment and decision on the administration of specifically requested product content in a specific package. This reduces the workload for system users and enables a transport vehicle can be sent directly to the current position where the required package or packages, which reduces the amount of unnecessary transport.

The invention also concerns a tracking device for a medical package, including fastening device for attachment to said package, an integral data logger which is arranged to record data during a time period for at least one environmental parameter that affects a specific product content lifetime. Tracking device includes: a calculation function which based on the logged data and time calculates an amount of the remaining lifetime of the contents of the package, an integrated indicator device which is arranged to indicate, at least on this specific product content, a residual lifetime, a communication device for receiving a signal to activate the indicator of any remaining lifetime by means of said indicator device. The tracking unit, to ensure that all relevant data relating to said specific product content, both input data and data generated by the data logger of that tracking device, can be handled and transferred, has a unique device identity that is readable, which can be interconnected with said unique identifier and said information on said package, whereby said unique device identity of the tracking device is readable by external means.

The invention also concerns a medical package provided with: at least one unique identifier and other relevant information, including at least a specification of the package product content and/or packing date, which identifies and characterizes a specific product content of that package, and a tracking device which is arranged to accompany said package with said specific product content over a period that extends from the input of said package, whereby the tracking device includes an integrated data logger, which is arranged to register data about at least one environmental parameter affecting that specific product content's lifetime during same period. The tracking unit includes a calculation function, which based on logged data and time calculates a value for said remaining lifetime. The tracking device includes an integrated indicator device which is arranged to indicate, at least on this specific product content, remaining lifetime, whereby the tracking device includes a communication device for receiving a signal to activate indication of any remaining lifetime by said indicator device. To ensure that all relevant data relating to said specific product content, both input data and data generated by the data logger of that tracking device, can be handled and transferred, the tracking unit has a unique device identity that is readable, which can be related with said unique identifier and said other relevant information on the said package, whereby said unique device identity of the tracking device is readable by external means.

The invention also concerns a method for managing medical package, whereby each individual package is provided with at least one unique identifier and other relevant information, including at least a specification of the package product content and/or packing date, which identifies and characterizes a specific product content of that package. The method comprises providing package with at least one tracking device which is arranged to accompany the package with said specific product content over a period that extends from the input of said package to a possible decision on administration of that specific product content to an intended recipient, whereby tracking device includes an integrated data logger, which is arranged that during the same period, record data on at least one environmental parameter affecting the specific product content lifetime. The method includes the steps of: to calculate a value for remaining lifetime by the tracking device and based on the logged data and time, indicating by means of the indicator of the tracking device, the at least specific product content's remaining lifetime, to activate indication of any remaining lifetime, to manage and transmit data relating to the specific product content, both input data and data generated by the data logger of that tracking device between the system units, has a unique device identity that is readable and associated with the unique identifier and said other relevant information on that package.

Other objectives, advantages and features of the present invention will become apparent from the following description, patent claims and the attached drawings

BRIEF DESCRIPTION OF THE DRAWINGS

In the following some embodiments of the invention are described in more detail, merely as an example and with reference to the attached schematic drawings, where.

DETAILED DESCRIPTION

In the following, a number of different embodiments of a system for handling medical packages according to the invention will be described in detail with reference to the appended FIGS. 1-5.

Figure 1:
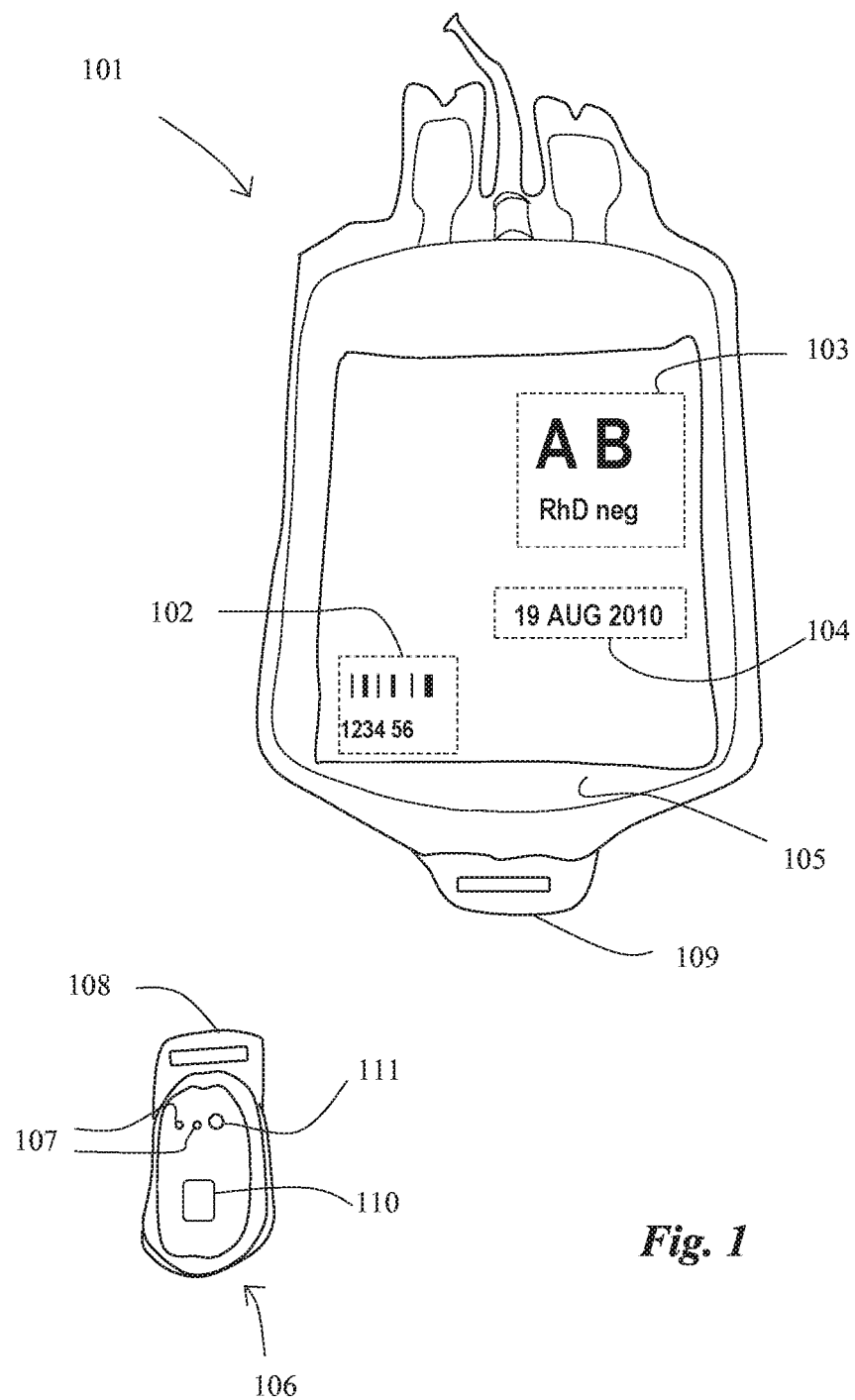
FIG. 1 is a schematic illustration of a medical package in the form of a blood bag, along with a tracking device as part of one embodiment of the system according to the invention, whereby the displayed tracking device is designed to accompany the blood bag during a period that extends from the input of the blood bag in the system to a possible decision on administration of blood in the blood bag to an intended recipient or a decision on disposal of blood bag.

FIG. 1 shows a schematic illustration of a medical package 101 in the form of a blood bag. The package 101 is handled in a system with a plurality of, figuratively speaking, similar package units and is therefore at its outer surface provided with a label with information, which at least includes a unique identity code 102 and other relevant information, 103, 104, which identifies and/or characterizes a specific product content 105 in the package 101 in a unique, for the use of the specific product content, necessary way. In the case of package 101 as shown in FIG. 1, the unique identity code 102 is a bar code that is intended to be read with a barcode scanner, combined with a bag number (corresponding bar code) that can be read visually by a system operator, to also allow for visual reading of the unique identity of the blood bag and input of it manually in the system if this for some reason is necessary. It should be noted that the information on the blood bag as shown in FIG. 1 is not identical to the information that would appear on an actual blood bag. For the simplicity reason, the information in the drawing is incomplete and schematic and only illustrated as a support for the present description.

With continued reference to FIG. 1, the system of the invention comprises at least one tracking device 106 arranged to accompany the package 101 with the specific product content 105 over a period of time that extends from the entry of the package 101 in the system to a possible decision on administration of the specific product content 105 to an intended recipient.

The tracking device 106 in the system according to the invention can be arranged to accompany the package 101 with the specific product content during the above time period in a number of different ways. In one embodiment of the invention, the tracking device 106 has a first fastening device 108 which is adapted to be attached to the second fastening device 109 of package 101, as shown in FIG. 1. The tracking device 106 may advantageously be arranged to accompany the package 101 by attaching it to the package by means of a strap, string, a rope or a chain. Alternatively, the tracking device is arranged to accompany the package by attaching it using an adhesive on the exterior of the package, or packaged in a preferably transparent exterior package common to the package.

The tracking device 106 in the system of the invention includes an integrated data logger/data storage device (not shown in the figures) which is arranged to, during above time period, record data about at least one environmental parameter that affects the specific product content's 105 remaining lifetime. The ambient parameters, which using an appropriate sensor device is logged continuously or at least regularly at frequent intervals, by the data logger are preferably at least the temperature of the environment where the package is. In such a case, the tracking device 106 includes one for this purpose suitable temperature sensor. The data logger can also be arranged to record data about several environmental parameters simultaneously, such as both temperature and moisture content, or to register any other parameter that is related to the environment, such as light conditions, and/or radiation, such as radioactive radiation, by sensing using one or more sensor devices.

To enable the continuous or regular data logging of ambient data, the tracking device 106 comprises, in one embodiment, an integrated power source (not shown in the drawings) with a capacity that is selected to ensure the data logger power supply throughout the aforementioned period. The power source can be of any suitable type whatsoever, but preferably is provided in the form of a battery, a fuel cell, or a capacitive energy source, such as a super capacitance. In one version, the battery or capacitance may be charged inductively.

The tracking device 106 according to the invention also includes a calculation function, including for example a calculation algorithm, which based on the logged data and time calculates a value for the remaining lifetime, for example, an estimated number of days remaining lifetime or a calculated expiration date of the product content that tracking device accompanies. Calculation algorithm has different form depending on which ambient parameter(s) that is/are logged, but primarily is based on prior knowledge about the durability of the type of product content available in the current package in relation to the environment parameter(s) logged by the data logger in the current tracking device. In the system according to the invention may therefore include individual tracking devices with different types of data logging and various algorithms if the system is designed to handle different types of package products whose contents are different in terms of storage characteristics. The system, which only will handle packages with product content of one main type (such as bags with transfusion blood) one could of course program the necessary computational algorithms in the tracking device from the start, but even in such cases it is advantageous for the system allowing entering new computational algorithms in the system's tracking device if this is necessary for some reason.

The tracking device 106 or tracking devices in the system according to the invention also includes an integrated indicator device 107, which is arranged to indicate to an operator, at least if the specific product content 105 in a package have a remaining lifetime or not. Advantageously, the integrated indicator device includes, as shown schematically in FIG. 1, one or more light emitting diodes (LEDs) 107 and/or a sound generator (not shown in the figures) that show or indicate to an operator whether the product content has remaining lifetime or not. Such an indicator device increases security of the system as the packages with the indicated completed useful lifetime of the product content can immediately be removed from the handling of the system by an operator for special control and discarded if it is necessary.

The integrated indicator device of the tracking device 106 may additionally or alternatively include a display 110, as indicated schematically in FIG. 1, primarily for the displaying an estimated remaining useful lifetime and/or an expiry date for the specific product content 105 in the current package. Such a display or indicator device is advantageous because the system operator can easily see the estimated remaining lifetime of each package and therefore use this information, e.g. when placing several packages in a cold room, or when choosing a specific package for administration to a recipient.

In one embodiment, where the tracking device 106 is arranged to accompany a package 101 containing a blood product 105, the integrated indicator device 110 is arranged to show a rejection indication if it has been exposed to an ambient temperature with a maximum and minimum value, so that this particular package can immediately be removed from the system and discarded by an operator when he or she becomes aware of cassation indication.

In one embodiment, the tracking device is configured with temperature ranges and can thus sett which maximum/ minimum temperature is required depending on the package content, region, demands, etc.

For example, in an application in which the package contains blood, the temperature range which is default in the tracking device can be according to Table 1:

TABLE 1

| Temperature | Hours remaining for which the blood is valid |
|---|---|
| <1° C. | 0 hours |
| <10° C. | 1008 hours |
| <24° C. | 24 hours |
| <30° C. | 4 hours |
| >=30° C. | 0 hours |

The table shows in the left column values for blood bags ambient temperature and the time left for which the blood is valid, in the right column.

Each tracking unit 106 of the system according to the invention has a unique device identity (not shown in the figures) that can be read and in the system it is connected with the unique identity code 102 and other relevant information, 103, 104 on the package 101 with which the tracking device accompanies, to ensure that all relevant data relating to the package-specific product content 105, both data input by the operator and the data generated by the data logger in the tracking device 106 or other system devices in the system, can be handled and transferred between the system devices without risk of confusion.

In one embodiment of the system according to the invention, the unique device identity of the tracking device 106 comprises a visible marking (not shown) which is arranged to be read visually by an operator. Such a visually readable marking on the tracking device, such as a unit number, provide especially when entering new products into the system, a higher level of security because a system operator can visually compare the label on the tracking device with an equally visually readable identity code of a package that is fed into the system for the first time. Such visually readable markings or data on the tracking devices and the package also provide an opportunity for cross-checking and thus greater safety for the continued management of package that is already entered in the system.

In one embodiment of the invention, the unique device identity of the tracking device 106 is also arranged to be read from an optical marking, such as a bar code, using an optical reader. The unique device identity of the tracking device 106 can alternatively or additionally be arranged to be read wirelessly via radio signals, infrared or capacitively. Preferably, the tracking device 106 includes an antenna for wireless transmission of data via radio waves or infrared or capacitive transmission. A capacitive readout of data can be achieved by two "transmitting" electrode plates, which are arranged inside the tracking unit's outer casing, brought close to two "receiving" electrode plates of another read system unit in the system of the invention.

In a particularly advantageous embodiment of the system according to the invention, the tracking device 106 is arranged for wireless transmission of data via radio waves over one or more of the frequency bands 900 MHz, 2.4 GHz, 5.2 GHz and/or 5.8 GHz. Radio communication over these bands is free worldwide and frequencies are also allowed to be use in hospitals.

Advantageously, the tracking device 106 includes a communication device 111 for receiving signals from an operator, e.g. for the reception of a signal from the operator to activate the display of any remaining lifetime of the tracking device's LEDs 107 or a display of a value of the estimated remaining lifetime on a display 110. The communication device can favorably be provided in the form of a capacitive or mechanical switch 111 and for example be in form of touch buttons, such as one or more foil buttons. The tracking device 106 may alternatively include a communication device in the form of a piezoelectric-crystal reacting to knock or motion. Such a communication device allows an operator to communicate with the tracking device, e.g. by knocking it into a table top, shake it, or the like.

The tracking device is preferably provided with an outer shell with no cracks, folds, grooves or moving parts to facilitate cleaning, and also for reuse of the tracking device in the system after reprogramming. The previously mentioned LEDs 107 are preferably arranged in translucent parts of the outer casing. The outer casing is preferably made of one or more suitable plastic material and has no metallic surfaces as these are difficult to keep clean and may corrode when cleaning and also could complicate passage of radio waves. In a particularly advantageous embodiment, the tracking device 106 has a fluid-tight casing, whereby components included in the tracking device have a design and made of materials that permit washing, preferably including centrifugation, in a conventional washing machine with a water based wash agent at a temperature above 70° C. This embodiment makes it possible to clean the tracking device in conventional, often existing equipment, and then be able to reuse the tracking device after a reprogramming of the same and updating its data into the computer system that keeps track of packages and their accompanying tracking devices.

Figure 4:
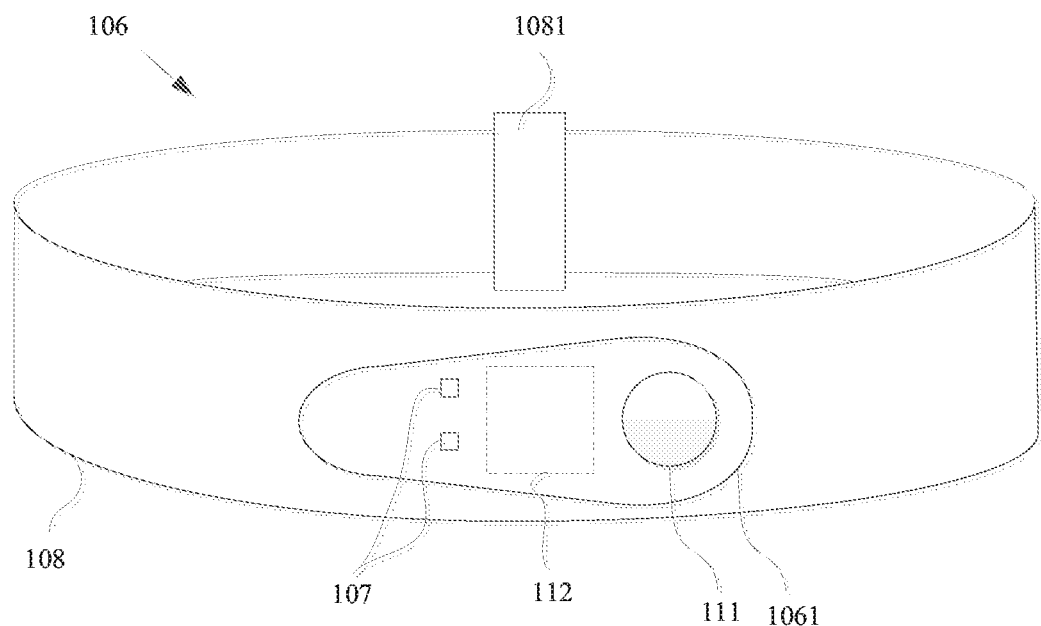
FIG. 4 illustrates schematically a second embodiment of a tracking device, according to the present invention.

FIG. 4 illustrates a second embodiment of the tracking device 106, including a housing 1061, indicating means 107, attaching device 108 and communications parts 111.

The outer casing 1061 of the housing is arranged with no crevices, folds, grooves or moving parts to facilitate cleaning, and that after reprogramming to reuse tracking device in the system. Indicating means 107 can be LEDs 107 with different colors and can be arranged under translucent parts of the outer casing. The outer casing is preferably made of one or more suitable plastic materials. Even here, the tracking device 106 has a fluid-tight casing, whereby the components of the tracking device have a design and made of material that allow cleaning. Attachment parts 108 are arranged as a band that can enclose the package. The band can be fitted with a locking device 1081 that may also allow modification of the strap length adjustment for different package sizes. The communication device 111 is intended for the reception of signals from a user or operator to activate the display for any remaining lifetime with the tracking device's LEDs 107 or a display for a value of the estimated remaining lifetime on a display (not shown). The communication device may be in the form of a capacitive or mechanical button or switch in the outer casing. Even this embodiment of the tracking device 106 may include a communication device in the form of a piezoelectric-crystal reacting to knock.

Figure 5:
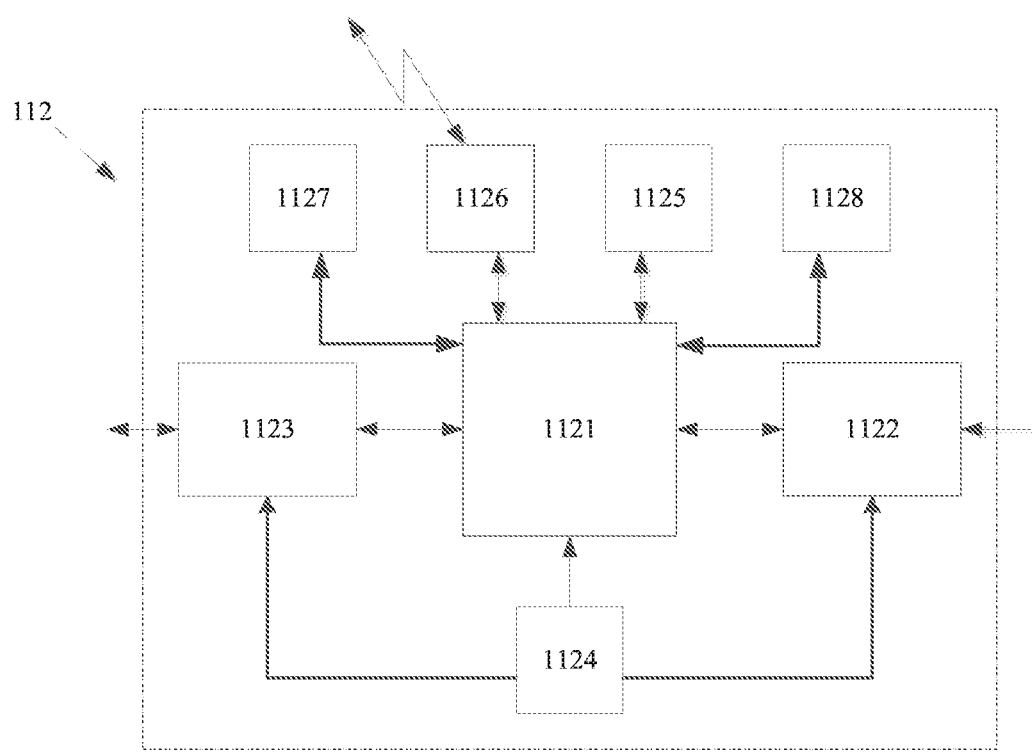
FIG. 5 illustrates schematically example of the electronics in a tracking device, according to the present invention.

112 designates the electronics of the tracking device. One or more power sources can be integrated with the electronics. FIG. 5 shows a schematic diagram of the electronics 112. The electronics may include a microprocessor 1121, one or more sensors 1122, interface 1123 and a power source 1124, a memory 1125, a communications unit 1126, and a motion detector 1127. The microprocessor 1121 is configured to, with respect to instructions stored in a memory 1125 or an internal memory, control the tracking device's functions, such as reading sensors, execute the measurement program, or indicate a fault or alarm.

The sensor(s) 1122 detects the parameters needed, such as temperature, radiation, humidity, pressure, pH value, etc. The interface 1123 is arranged to read the incoming instructions, e.g. from the button 111 and operate the indicator system. The memory 1125 may include instructions to the processor and/or store data. The communication unit 1126 is arranged to communicate with the outside world, wireless or wired, e.g. using WiFi, Bluetooth, IR, RF, RFID, etc.

Figure 2:
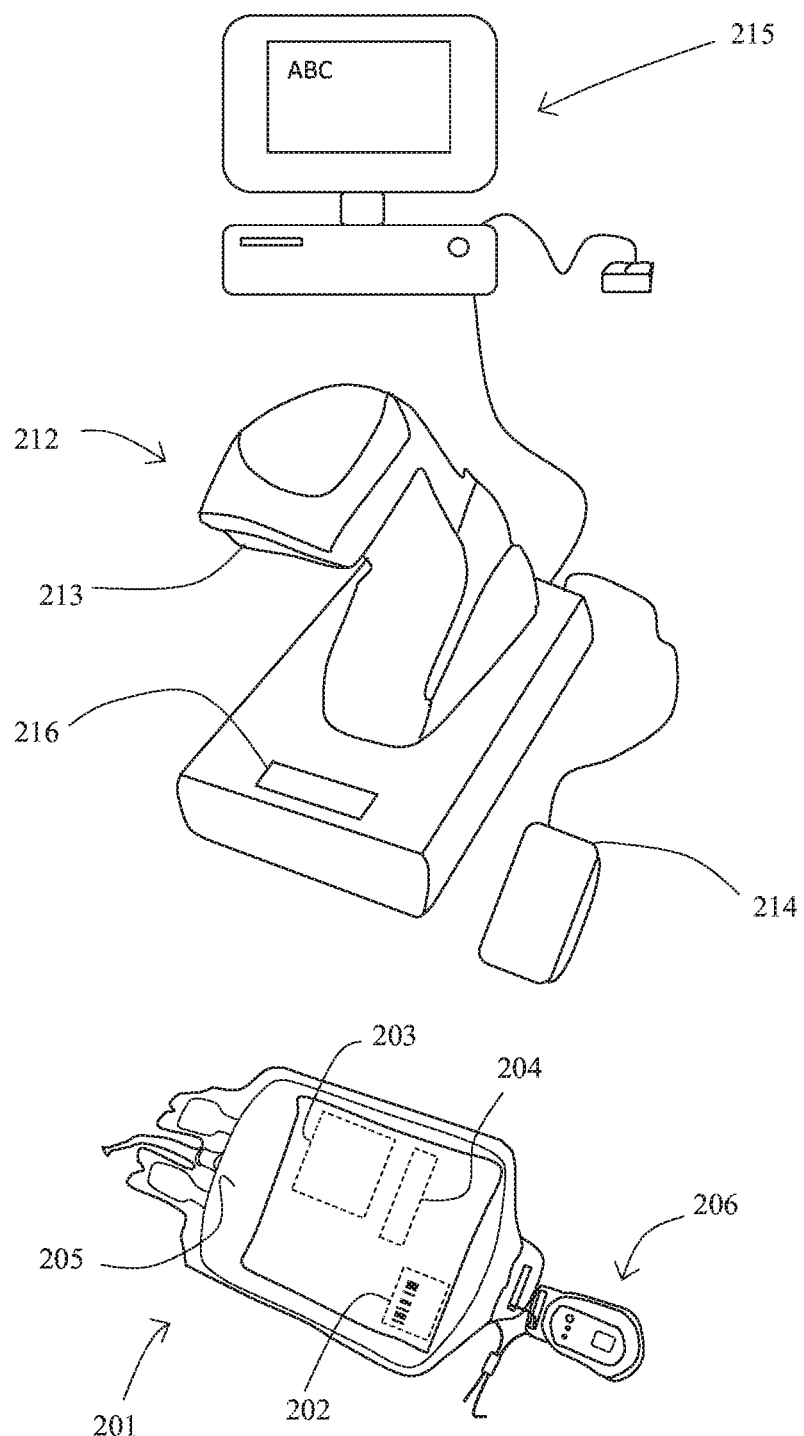
FIG. 2 is a schematic illustration of an access point as part of one embodiment of the system according to the invention, along with a blood bag with an included tracking device according to the invention.

In one embodiment of the system according to the invention, illustrated schematically in FIG. 2, the aforementioned other system devices in the system comprise at least one access point 212 which, for the entry of new medical package in the system, is provided with means for reading the unique identity code 202 and the other relevant information, 203, 204 on a specific package 201 and means for transmitting the identity code and information to at least one data record in a database included in the system, and also means for reading the unique device identity of a tracking device 206 which will accompany the specific package 201 in the continued management of the system and means for transmission of this unique device identity to the database to be linked with the above data item or data items.

In another embodiment of the system according to the invention, the above-mentioned other system devices in the system comprise at least one access point 212 which, for the handling of medical package that is already entered into the system without risk of confusion and updating of data on package and location of the system, is provided with means for reading the unique device identity of each tracking device 206 included a specific package whose previous data already exists at least as one data record in the aforementioned database before the package 201 can continue in the system, past the access point.

In another embodiment of the system according to the invention, the above-mentioned other system devices in the system comprise at least one access point 212 which for the retrieval and updating of data on at least one environmental parameter that affects the remaining lifetime of a specific package product content, is provided with means for reading any new data relating to the at least one environmental parameter recorded by the data logger with each tracking device 206 accompanying a specific package, whose previous data already exists as last one data record in the aforementioned database, when this specific package 201 passes the access point 212.

It should be noted that the above three functions, which can be performed by an access point may be provided separately by different access points that are located in different parts of the system, and that there may be access points in the system which are equipped with several features, or can perform all three functions.

Each access point 212 in the system according to the invention preferably comprises at least one optical scanner 213, preferably a laser scanner for barcode or quick response code or a camera, for reading the unique identifier 202 and other relevant information, 203, 204 on a specific packing 201.

Each access point 212 in the system according to the invention preferably also includes at least one wireless reader 214 for radio signals, infrared, or capacitive readout of the unique device identity of a tracking device 206 which will be supplied with or accompanying a specific packing two hundred and first Access point 212 in the system according to the invention can also with advantage include at least one wireless reader 214 for radio signals, infrared, or capacitive readout of that data on at least one ambient parameter recorded by the logger with a tracking device 206 which accompanies a specific package 201. This embodiment makes it possible to read the current estimated remaining lifetime of the product content of that specific package each time the package passes such an access point, thereby allowing retrieval of latest estimated remaining lifetime as possible to a central computer system.

The access point 212 in the system according to the invention can with advantage include at least one communication link to a server, preferably of type LAN (Ethernet), wireless LAN, GSM or GPRS, for transmitting data between the access point 212 and the server and/or other system devices in the system.

The access point 212 in the system according to the invention can with advantage include at least one (local) computer device 215 arranged to handle reading, processing and communication of information in the system, and communication with an operator.

Each access point 212 in the system according to the invention preferably comprises at least one indicator device for communication with an operator, preferably including LED/illumine surfaces, a display 216 and/or a sound generator. The access point 212 in the system according to the invention can also with advantage include at least one communication means (not shown in the drawings), preferably in form of a capacitive or mechanical key or an piezoelectric-crystal reacting to knock, which can be affected by an operator.

Figure 3:
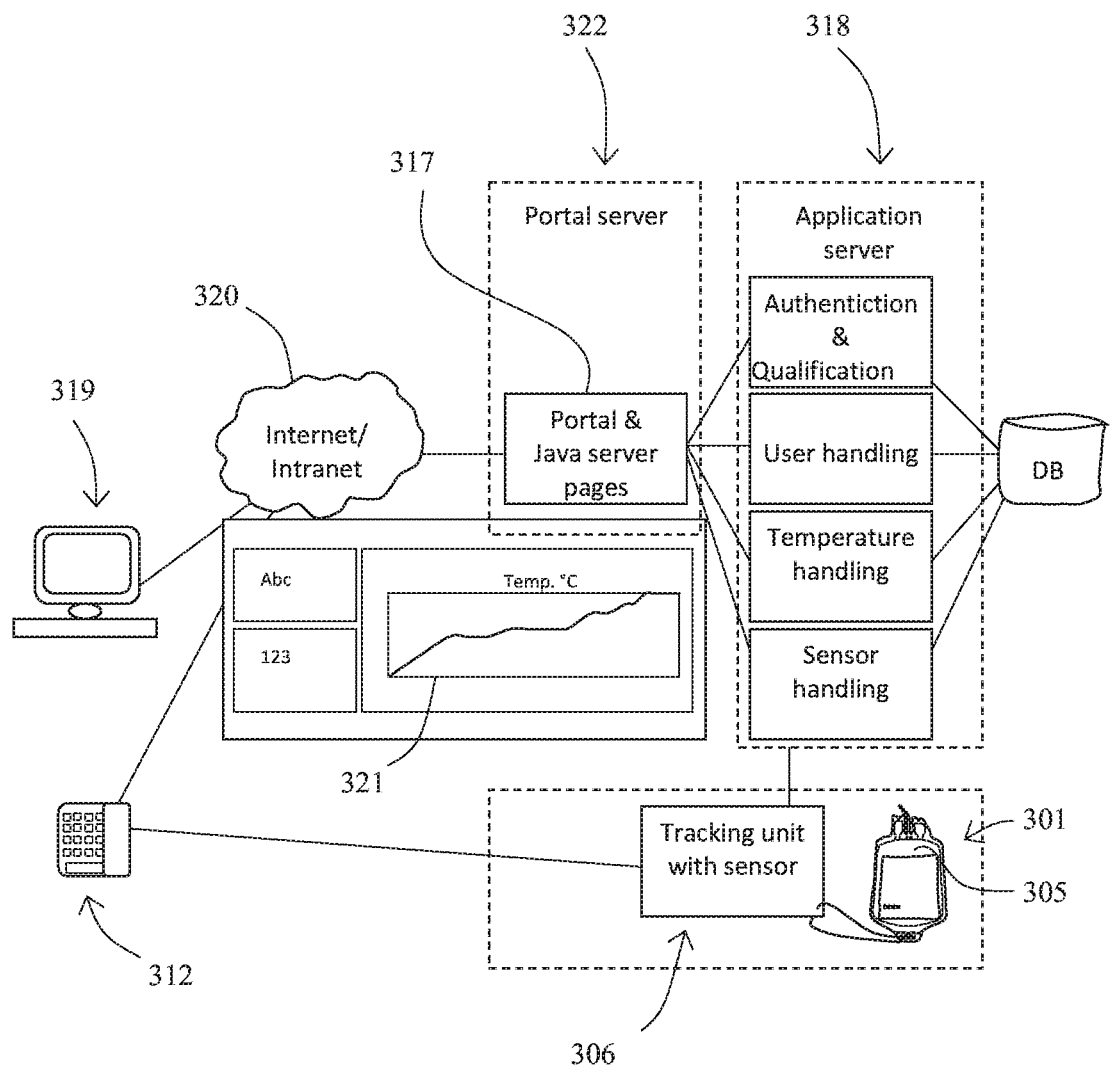
FIG. 3 is a schematic block diagram of the structure of one embodiment of the system according to the invention.

In one embodiment of the system, according to the invention, schematically illustrated in FIG. 3, the aforementioned other system devices in the system comprise at least one portal 317 for system users who can communicate with at least one data server 318 that stores data relating to all medical packages that are entered into the system. Provision of such an access point 317 enables the system users to access these data from a system user selectable location. The data stored in the data server in this embodiment includes at least: a unique identifier for each specific package 301 inserted into the system, a unique device identity for the specific detection unit 306 that comes with this specific package in the management of the system, a latest reading date of the information concerning the specific package 301 stored in the data server 318, a specification of the last access point 312 as the specific detection unit 306 and thus the specific package 301 has passed through the system, an estimated expiration date for a specific product content 305 in the specific package 301, and other relevant information that identifies and characterizes the specific product content 305 in a unique, for the use of the specific product content necessary way, which data the system users may access from at least one user terminal 319 which is connected to the portal 317 for system users. The system according to this embodiment allows system users to be able to find a specific package or one product content as requested, to follow this specific package or this specific product content movement and current location in the system, and to be able to consult a calculated expiration date for the specific product content of a specific package.

The portal 317 for system users includes preferably at least a search function, which is provided to permit search for packages 301 in the system containing the specific product content 305 and the estimated remaining lifetime of a specific user needs, as well as search for specific packages 301 that are physically located close to the specific user. The search function is preferably accessible from a terminal 319 via the Internet 320 or intranet.

In case of blood packages, for example, the portal may allow for search of:
All tracking data in one place;
Search for specific blood type, specific status, specific location, etc.;
See Check-in Nodes' location on a map;
Warnings about blood soon to expire;
Open complete temperature log for each tracer/blood bag—export logs;
Preferably, the portal 317 for system users also allows access to a detailed storage history of a specific package, preferably a temperature history 321, obtained from the ambient parameter data recorded by the integrated data logger in the tracking device 306 during the period of time the tracking device is shipped with the specific package 301 when handled in the system.

The data for medical package 301 that can be accessed via the portal 317 for system users can be saved in separate data records stored in multiple databases and/or servers 318, 322 and/or computers, whereby these separate data records are linked in the system to give the system user, user-friendly access to all relevant data concerning a specific product content 305 in a specific package 301 without risk of confusion.

The enclosed hardware and software in the system can with advantage be particularly fitted for handling packages containing a specific product, such as blood products 301, or for handling vaccine package.

Back to FIG. 5, one embodiment, the tracking device may comprise a configurable alarm function, which detects motion of the detector and package using the motion detector 1127 to ensure that the monitored package requirement for a specific position mode, such as "no-movement/horizontal motion/vertical motion/shocks" is fulfilled. The system may thus be configured to generate an automatic alarm when the requirements are not fulfilled and send an alarm message to a responsible entity via mail, sms, mobil app or other informative media.

In one embodiment, the detector 1122 of the tracking device may comprise a pressure sensor to detect ambient pressure. In environments where shipments can be carried out under pressure, the system with pressure sensor provides opportunity to establish that set values are followed.

In one embodiment, the detector 1122 may comprise sensors for measuring pH and oxygen content. Consequently, pH value and oxygen contents are measured in the monitored fluid product, for example blood bag, and an alarm is raised if values exceed predetermined values. According to one embodiment the tracking device may comprise an optical sensor on one side facing the package, which can illuminate the content (using IR, laser, etc.) and analyze the reflection to measure pH and/or oxygen content or any other relevant parameter.

The device may also comprise sensors for gas or liquid analyzes for the packaged media of a monitored product, the system may determine that a shipment of a drug/biological material has been within the frameworks set up for the product. The system may be configured so that the automatic alarm is sent when the regulations are not followed.

The device may comprise a positioning unit (GPS, GLASNOSS, etc.) 1128 or use position information from external devices, to report location along the transportation chain. The system users (using portals) can from a selectable spot access all the data required for identification, tracking, positioning, ordering, transportation, quality assessment and decision on the administration of specifically requested product content in a specific package. This reduces the workload for system users and enables a transport vehicle can be sent directly to the current position where the required package or packages, which reduces the amount of unnecessary transport.

The tracking device may store and communicate the date and time information to a central database when the patient is given or end given blood/medicine using WiFi, Bluetooth, IR, RF, RFID, NFC, etc., communicating with mobile devices or gateways. The system may be configured to a patient based on a doctor's prescription to validate that the prescription compliance.

The system may contain exsanguination information and blood type, etc. and when blood is transfused to a patient, the data such as blood type is retrieved, using a device that validates the blood group against a patients registered and thereby guarantees that the patient receives the correct blood type.

The system according to the invention comprises a number of access points that are located at least at the exit of a unit that makes or fills medical package with specific product content, at the entrance to a depot or an intermediate storage where the packages are stored, at the exit of the depot, or intermediate storage, and at the entrance to a treatment or care facility in which the administration of the specific product content is done.

The system according to the invention can with advantage include at least one access point in a transport vehicle designed to transport packages from a manufacturing or filling unit to a terminal or an intermediate storage, or from the depot or from the storage to a treatment or care facility, from the treatment or care facility to another treatment or care facility, from the treatment or care facility back to the depot or the intermediate storage, or from this treatment or care facility to another depot or another intermediate storage. The system according to the invention may thus comprise at least one access point on board a car, an ambulance, a truck, a trailer truck, an airplane, a helicopter, a boat or a ship, or a portable access point that can be transported to a desired position by an operator. One or more portable access points can with advantage used in the establishment of a system according to the invention of a disaster or war situations.

In the above, a number of different embodiments of the invention have been described with reference to the illustrations on the attached drawings. It must be understood that the described embodiments and details of the drawings alone should be seen as an example and that number of other embodiments of the invention are possible in the context of the attached patent claims.

Within the scope of the invention are also embodiments in which the system includes devices for detection, reading and/or logging of possible contamination of package, for example, in an embodiment in which at least one access point in the system has a specially designed scanner that uses laser scans of a specific package or tracking device reflectance and/or transmission within a particular wavelength range before the package with its accompanying tracking device is allowed to pass the access point. This embodiment of the system according to the invention allows the packages discovered to be contaminated, can be removed from the system and discarded.

What is claimed is:

1. A system for handling medical packages, in which each individual package is provided with at least one unique identifier and information comprising at least one specification about at least the packaged product content or packaging date, used for one or several of identification or characterization of a specific product content of the package, the system comprising:

at least one tracking device, configured to accompany the package over a period of time extending from the registration of said package in the system to a possible decision on administration of the specific product content to an intended recipient, the tracking device comprising:

an integrated data logger arranged to record data during said period of time about at least one environmental parameter that affects lifetime of said specific product content, a processor configured to calculate a value for said remaining lifetime based on the logged data and time, an integrated indication device, which is arranged to indicate, at least about the specific product contents remaining lifetime, a communication device for receiving a signal to activate indication of any remaining lifetime with said indication device, a unique visual package identity readable by an operator and in the system associated to a unique identity code of tracking device and other relevant information on said package, to ensure that data relating to the specific product content, both input data and data generated by the data logger of the tracking device or by other system devices in the system, can be handled and transferred between said system units, an accelerometer configured to detect a specific motion of the package, wherein the specific motion comprises a knocking of the package against an object or a shaking of the package;

when the specific motion is detected by the accelerometer, the processor is further configured to generate instruction for handling the package based on the detected motion, an optical sensor positioned on one side of the tracking device facing the package, the optical sensor being configured to illuminate the content of the package and analyze a reflection from the content of the package to measure pH and/or oxygen content;

at least one arrangement for reading said unique visual package identity, and at least one arrangement for reading said unique identity code of the tracking device; and a laser scanner in an access point configured to at least one of detect, read or log contamination of the package, the laser scanner using laser scans to scan a specific package or tracking device reflectance and/or transmission within a particular wavelength range before the package with its accompanying tracking device is allowed to pass the access point.

2. System according to claim 1, wherein the tracking device attached to package through one or several of:

tracking device comprises a first fastening device adapted to be attached to the second fastening device of the package, attached together with the package with help of a strap, a band, a rope or a chain attached by means of an adhesive on exterior of the package and/or packaged in common, preferably transparent, outer packaging.

3. System according to claim 1, wherein the tracking device comprises at least one sensor device arranged for sensing one or several of ambient temperature, moisture content, light conditions, or radiation, such that one or more of said parameters can be recorded by said data logger.

4. System according to claim 1, wherein the tracking device comprises an integrated power supply with a capacity that is selected to ensure the data logger powered throughout said period of time.

5. System according to claim 1, wherein the tracking device comprises an integrated power source in form of a battery, a fuel cell, or a capacitance.

6. System according to claim 1, wherein the indication device of the tracking device includes one or more of the light emitting diodes, a sound generators or a display, primarily for reproducing the estimated remaining lifetime of the specific product content.

7. System according to claim 1, wherein the tracking device is arranged to accompany a package containing a blood product, and the integrated indicator device is arranged to show a cassation indication if the product has been exposed to an ambient temperature between a maximum and a min value.

8. System according to claim 1, wherein the tracking device comprises a communication portion for receiving signals.

9. System according to claim 1, wherein the tracking device comprises a communication portion in form of one or more of capacitive, mechanical switch or a piezoelectric-crystal, which reacts to movement.

10. System according to claim 1, wherein the unique visual package identity of the tracking device comprises a visible mark arranged to be read visually.

11. System according to claim 1, wherein the unique visual package identity of the tracking device is arranged to be read by an optical device, using an optical reader and/or wirelessly via radio signals, infrared or capacitively.

12. System according to claim 1, wherein the tracking device comprises a fluid-tight casing, and that the components of the tracking device are designed and made of materials that allow cleaning in a conventional washing machine with a water based wash agent at a temperature above 70° C.

13. System according to claim 1, wherein said other system devices in the system includes at least one access point, which for the entry of new medical package in the system is equipped with means for reading said unique visual package identity and that other relevant information on a specific package and arrangement for transmitting said identifier and information to at least one data record in a database included in the system, and means for reading said unique visual package identity of a tracking device that will accompany the specific package for the continued handling of the system and means for transmitting said unique visual package identity to said database for association to said data record or data records.

14. System according to claim 1, wherein said other system devices in the system comprise at least one access point which, for the handling of medical package that already is entered into the system and to update the data on said package and position in the system, is equipped with means for reading said unique visual package identity of each tracking device accompanying a specific package whose previous data already exists as at least one data record in said database before said package is passed on in the system past said access point.

15. System according to claim 1, wherein said other system devices in the system comprise at least one access point which, for the retrieval and updating of data about at least one environmental parameter that affects the remaining lifetime of a specific package product content, is provided with means for reading any new data on said at least one environmental parameter recorded by the data logger at each tracking device accompanying a specific package, whose previous data already exists as at least one data record in said database when said specific package passes said access point.

16. System according to claim 1, wherein the access point comprises one or several of:

at least one optical reader, comprising one of a laser scanner for barcode or quick access code or a camera, for reading said unique visual package identity and that other relevant information on a specific package;

at least one wireless reader for radio signals, infrared, or capacitive readout of said unique visual package identity of a tracking device, which accompanies a specific package;

at least one wireless reader for radio signals, infrared, or capacitive readout of the data about at least one environmental parameter recorded by the logger with a tracking device provided with a specific package;

at least one communication link to a server, preferably LAN (Ethernet), wireless LAN, GSM or GPRS, for transmitting data between said access point and server or other system devices to the system;

at least one computer device arranged to handle reading, processing and communication of information in the system, and communication with an operator;

at least one indication device for communication with an operator, preferably comprising light emitting diode/light panel, a display and/or a sound generator;

at least one communication device, preferably in form of a capacitive or mechanical key or a piezoelectric-crystal that responds to tapping, which can be affected by an operator; or at least one communication device, preferably in form of a capacitive or mechanical key or a piezoelectric-crystal which responds to tapping, which can be affected by an operator.

17. System according to claim 1, wherein said other system devices in the system include at least one access point for system users who can communicate with at least one data server that stores data relating to all medical package that is entered into the system, whereby said data stored in said data server comprises one or several of:

a unique identifier for each specific package, which is inserted into the system, a unique visual package identity for the specific detection unit that accompanies the specific package in the handling of the system, a latest read date of the information concerning the specific package stored in said data server, a specification of the last access point, which said specific tracking device and thus the specific packing has passed into the system, an estimated expiration date for a specific product content of the specific package, and additional relevant information that identifies and characterizes the specific product content in a unique, for the use of that specific product content necessary means, which data the system users may access from at least one user terminal connected to said portal for system users.

18. System according to claim 17, wherein the access point for system users include at least one search function accessible from said terminal, Internet or an intranet.

19. System according to claim 1, wherein the system comprises a number of access points that are located at least:

at an exit of a device that makes or fills medical package with product-specific content, at an entrance to a depot or an intermediate storage where said packages are stored, at an exit from the said depot or the store, or at an entrance to a treatment or care facility, in which the administration of the specific product content is carried out.

20. System according to claim 1, wherein the system comprises at least one access point in a transport vehicle designed to transport packages from a manufacturing or filling unit to a depot or an intermediate storage, or from said depot or the store to a treatment or health care unit, from said treatment or care facility to another treatment or care facility, from the treatment or care facility back to the depot or store, or from that treatment or care facility to another depot or another intermediate storage.

21. System according to claim 1, wherein the system comprises at least one access point on board a car, an ambulance, a truck, a trailer truck, an airplane, a helicopter, a boat or a ship, or a portable access point that can be carried to a desired position by an operator.

22. System according to claim 1, wherein the tracking device comprises a detector comprising a pressure sensor to detect ambient pressure.

23. System according to claim 1, wherein the tracking device comprises sensors for gas or liquid.

24. System according to claim 1, wherein the tracking device comprises a positioning unit.

25. System according to claim 1, wherein the tracking device is configured to store and communicate date and time information to a central database when a patient is administered content of the package.

26. System according to claim 1, comprising exsanguination and blood information and when blood is transfused to a patient, the data such as blood type is retrieved, using a device that validates the blood group with respect to a patient's registered information.

27. A tracking device for a medical package, comprising:

fastening device for attaching to said package an integrated data logger, which is configured to record data about at least one environmental parameter that affects a specific product content lifetime over a period of time, a processor configured to calculate a value for a remaining lifetime of the package content based on the logged data and time, an integrated indication device, which is arranged to indicate, at least about the specific product content remaining lifetime, a communication device for receiving a signal to activate the indication of any remaining lifetime of said indicator device, a unique device identity, which can be associated with a unique identity code of the tracking device to ensure that all relevant data relating to said specific product content, both input data and data generated by the data logger of the tracking device, an optical sensor positioned on one side of the tracking device facing the package, the optical sensor being configured to illuminate the content of the package and analyze a reflection from the content of the package to measure pH and/or oxygen content;

an accelerometer configured to detect a specific motion of the package, wherein the specific motion comprises a knocking of the package against an object or a shaking of the package;

when the specific motion is detected by the accelerometer, the processor is further configured to generate instruction for handling the package based on the motion detected; and an arrangement for tracking device reflectance and/or transmission within a particular wavelength range to be scanned by a laser scanning device in an access point configured to at least one of detect, read or log contamination of the package, the laser scanning device using laser scans to scan a specific package or tracking device reflectance and/or transmission within a particular wavelength range before the package with its accompanying tracking device is allowed to pass the access point.

28. A tracking device for a medical package, comprising:
fastening device for attaching to said package an integrated data logger, which is configured to record data about at least one environmental parameter that affects a specific product content lifetime over a period of time,
a processor configured to calculate a value for a remaining lifetime of the package content based on the logged data and time,
an integrated indication device, which is arranged to indicate, at least about the specific product content remaining lifetime,
a communication device for receiving a signal to activate the indication of any remaining lifetime of said indicator device,
a unique device identity, which can be associated with a unique identity code of the tracking device to ensure that all relevant data relating to said specific product content, both input data and data generated by the data logger of the tracking device,
a fluid-tight casing, and the components of the tracking device are designed and made of materials that allow cleaning in a conventional washing machine with a water based wash agent at a temperature above 70° C.;
an accelerometer configured to detect a specific motion of the package, wherein the specific motion comprises a knocking of the package against an object or a shaking of the package;
an optical sensor positioned on one side of the tracking device facing the package the optical sensor being configured to illuminate the content of the package and analyze a reflection from the content of the package to measure pH and/or oxygen content;
when the specific motion is detected by the accelerometer, the processor is further configured to generate instruction for handling the package based on the motion detected; and
a reflectance arrangement and/or transmission arrangement within a particular wavelength range to be scanned by a laser scanning device in an access point configured to at least one of detect, read or log contamination of the package, the laser scanning device laser scans to scan a specific package or tracking device reflectance and/or transmission within a particular wavelength range before the package with its accompanying the tracking device is allowed to pass the access point.

29. A system for handling medical packages, in which each individual package is provided with at least one unique identifier and information comprising at least one specification about at least the packaged product content or packaging date, used for one or several of identification or characterization of a specific product content of the package, the system comprising:
at least one tracking device, configured to accompany the package over a period of time extending from the registration of said package in the system to a possible decision on administration of the specific product content to an intended recipient, the tracking device comprising:
an integrated data logger arranged to record data during said period of time about at least one environmental parameter that affects lifetime of said specific product content,
a processor configured to calculate a value for said remaining lifetime based on the logged data and time,
an integrated indication device, which is arranged to indicate, at least about the specific product contents remaining lifetime,
a communication device for receiving a signal to activate indication of any remaining lifetime with said indication device,
a unique visual package identity readable by an operator and in the system associated to a unique identity code of tracking device and other relevant information on said package, to ensure that data relating to the specific product content, both input data and data generated by the data logger of the tracking device or by other system devices in the system, can be handled and transferred between said system units,
an optical sensor positioned on one side of the tracking device facing the package the optical sensor being configured to illuminate the content of the package and analyze a reflection from the content of the package to measure pH and/or oxygen content;
at least one arrangement for reading said unique visual package identity, and at least one arrangement for reading said unique identity code of the tracking device; and
a laser scanner in an access point configured to at least one of detect, read or log contamination of the package, the laser scanner using laser scans to scan a specific package or tracking device reflectance and/or transmission within a particular wavelength range before the package with its accompanying tracking device is allowed to pass the access point.

30. A tracking device for a medical package, comprising:
fastening device for attaching to said package an integrated data logger, which is configured to record data about at least one environmental parameter that affects a specific product content lifetime over a period of time,
a processor configured to calculate a value for a remaining lifetime of the package content based on the logged data and time,
an optical sensor positioned on one side of the tracking device facing the package the optical sensor being configured to illuminate the content of the package and analyze a reflection from the content of the package to measure pH and/or oxygen content;
an integrated indication device, which is arranged to indicate, at least about the specific product content remaining lifetime,
a communication device for receiving a signal to activate the indication of any remaining lifetime of said indicator device,
a unique device identity, which can be associated with a unique identity code of the tracking device to ensure that all relevant data relating to said specific product content, both input data and data generated by the data logger of the tracking device; and
a reflectance arrangement and/or transmission arrangement within a particular wavelength range to be scanned by a laser scanning device in an access point configured to at least one of detect, read or log contamination of the package, the laser scanning device being configured to scan a specific package or tracking device reflectance and/or transmission within a particular wavelength range before the package with its accompanying the tracking device is allowed to pass the access point.

31. A tracking device for a medical package, comprising:
fastening device for attaching to said package an integrated data logger, which is configured to record data about at least one environmental parameter that affects a specific product content lifetime over a period of time,
a processor configured to calculate a value for a remaining lifetime of the package content based on the logged data and time,
an integrated indication device, which is arranged to indicate, at least about the specific product content remaining lifetime,
a communication device for receiving a signal to activate the indication of any remaining lifetime of said indicator device,
a unique device identity, which can be associated with a unique identity code of the tracking device to ensure that all relevant data relating to said specific product content, both input data and data generated by the data logger of the tracking device,
an optical sensor positioned on one side of the tracking device facing the package, the optical sensor being configured to illuminate the content of the package and analyze a reflection from the content of the package to measure pH and/or oxygen content, and
a reflectance arrangement and/or transmission arrangement within a particular wavelength range to be scanned by a laser scanning device in an access point configured to at least one of detect, read or log contamination of the package, the laser scanning device using laser scans to scan a specific package or tracking device reflectance and/or transmission within a particular wavelength range before the package with its accompanying the tracking device is allowed to pass the access point.

32. A system for handling medical packages, in which each individual package is provided with at least one unique identifier and information comprising at least one specification about at least the packaged product content or packaging date, used for one or several of identification or characterization of a specific product content of the package, the system comprising:
at least one tracking device, configured to accompany the package over a period of time extending from the registration of said package in the system to a possible decision on administration of the specific product content to an intended recipient, the tracking device comprising:
an integrated data logger arranged to record data during said period of time about at least one environmental parameter that affects lifetime of said specific product content,
a processor configured to calculate a value for said remaining lifetime based on the logged data and time,
an integrated indication device, which is arranged to indicate, at least about the specific product contents remaining lifetime,
a communication device for receiving a signal to activate indication of any remaining lifetime with said indication device,
a unique visual package identity readable by an operator and in the system associated to a unique identity code of tracking device and other relevant information on said package, to ensure that data relating to the specific product content, both input data and data generated by the data logger of the tracking device or by other system devices in the system, can be handled and transferred between said system units,
an accelerometer configured to detect a specific motion of the package, wherein the specific motion comprises a knocking of the package against an object or a shaking of the package;
when the specific motion is detected by the accelerometer, the processor is further configured to generate instruction for handling the package based on the detected motion,
an optical sensor positioned on one side of the tracking device facing the package, the optical sensor being configured to illuminate the content of the package and analyze a reflection from the content of the package to measure pH and/or oxygen content;
at least one arrangement for reading said unique visual package identity, and at least one arrangement for reading said unique identity code of the tracking device; and
a laser scanner in an access point configured to at least one of detect, read or log contamination of the package, the laser scanner using laser scans to scan a specific package or tracking device reflectance and/or transmission within a particular wavelength range before the package with its accompanying tracking device is allowed to pass the access point, and
an interface for system users configured to provide search for a package in the system containing a specific product content and the estimated remaining lifetime of a specific user need and a package that is physically located close to the user.

33. The system of claim 32, comprising a number of access points located at least at:
an exit of a unit that makes or fills the package with specific product content,
an entrance to a depot or an intermediate storage where the packages are stored,
an exit of a depot, or intermediate storage,
an entrance to a treatment or care facility in which the administration of the specific product content, or
in a transport vehicle designed to transport the package.

34. The system of claim 33, wherein the access point is mobile.

* * * * *